United States Patent
Katsuki et al.

(10) Patent No.: US 10,228,341 B2
(45) Date of Patent: Mar. 12, 2019

(54) BIOSENSOR

(71) Applicants: ARKRAY, Inc., Kyoto (JP); Ultizyme International Ltd., Tokyo (JP)

(72) Inventors: Koji Katsuki, Kyoto (JP); Megumi Saeda, Kyoto (JP); Junko Shimazaki, Tokyo (JP)

(73) Assignees: ARKRAY, Inc., Kyoto (JP); Ultizyme International Ltd., Tokyo (JP)

( * ) Notice: Subject to any disclaimer, the term of this patent is extended or adjusted under 35 U.S.C. 154(b) by 0 days.

(21) Appl. No.: 15/294,396

(22) Filed: Oct. 14, 2016

(65) Prior Publication Data
US 2017/0108459 A1   Apr. 20, 2017

(30) Foreign Application Priority Data

Oct. 15, 2015   (JP) .................................. 2015-204035
Oct. 5, 2016    (JP) .................................. 2016-196904

(51) Int. Cl.
*G01N 27/327* (2006.01)
*C12Q 1/00* (2006.01)

(52) U.S. Cl.
CPC ......... *G01N 27/3272* (2013.01); *C12Q 1/006* (2013.01)

(58) Field of Classification Search
CPC ........................... G01N 27/3272; C12Q 1/006
See application file for complete search history.

(56) References Cited

U.S. PATENT DOCUMENTS

| | | | |
|---|---|---|---|
| 6,773,564 B1 * | 8/2004 | Yugawa | C12Q 1/006 204/403.14 |
| 2002/0042065 A1 * | 4/2002 | Han | A61B 5/14532 435/6.11 |
| 2005/0269214 A1 | 12/2005 | Lee | |
| 2009/0236222 A1 * | 9/2009 | Murase | C12Q 1/004 204/403.14 |
| 2009/0321277 A1 | 12/2009 | Heller et al. | |
| 2011/0069108 A1 * | 3/2011 | Fukuda | B41M 5/0023 347/20 |
| 2012/0097194 A1 * | 4/2012 | McDaniel | A01N 63/02 134/26 |

FOREIGN PATENT DOCUMENTS

| | | |
|---|---|---|
| AU | 644059 B2 | 12/1993 |
| EP | 2012121 A1 | 1/2009 |
| EP | 3078965 A1 | 10/2016 |
| EP | 3086113 A1 | 10/2016 |
| JP | 2901678 B2 | 3/1992 |
| JP | 2901678 B2 | 6/1999 |
| WO | 2013/144255 A1 | 10/2013 |

OTHER PUBLICATIONS

Extended European Search Report issued in corresponding European Patent Application No. 16194032.5 dated Feb. 20, 2017.
Office Action issued in corresponding European Patent Application No. 16194035.5 dated Aug. 3, 2018.

* cited by examiner

*Primary Examiner* — J. Christopher Ball (74) *Attorney, Agent, or Firm* — Morgan, Lewis & Bockius LLP (57) ABSTRACT

A biosensor includes a plurality of electrodes including a working electrode, and a detection layer which is immobilized on the working electrode and contains a crosslinking agent, an electrically conductive macromolecule and an enzyme transferring and receiving electrons to and from the working electrode. The working electrode is in an open system.

14 Claims, 8 Drawing Sheets

BIOSENSOR

CROSS-REFERENCE TO RELATED APPLICATION

This application claims the benefit of Japanese Patent Application No. 2015-204035 filed on Oct. 15, 2015 and No. 2016-196904 filed on Oct. 5, 2016 in the Japanese Patent Office, the disclosure of which is herein incorporated in its entirety by reference.

FIELD

The present invention to a disposable biosensor.

BACKGROUND

Disposable biosensors conventionally used are those obtained by applying a reagent containing an enzyme and a mediator to an electrode system disposed on a base material and forming a capillary to draw a liquid sample thereinto using a spacer and a cover (e.g., Patent document 1). The application of voltage to the biosensor enables the concentration measurement of a substance to be measured in a sample based on a diffusion current by the mediator.
[Patent document 1] Japanese Patent No. 2901678

SUMMARY

A disposable biosensor, for example, a glucose sensor, allows a specimen (a liquid sample) drawn into a capillary to dissolve and diffuse a reagent and detects the electric current generated by an enzyme reaction as the response electric current. For this reason, sensitivity of the glucose sensor is affected by the diffusion condition of the substance in the reagent. The dimensions (particularly the height) and volume of a capillary are defined so that inconsistencies of the reagent diffusion condition by the specimen are not caused between sensors.

However, the formation of a capillary needs components such as a spacer and a cover to be laminated on a base plate, and the presence of these components is a factor for increasing manufacturing costs of the biosensors. In the biosensor with a capillary, a specimen is brought closer to a suction opening of the capillary to introduce the specimen into the capillary. However, a suitable amount of the specimen is not introduced into the capillary depending on the way a user handles the biosensor, thereby a concentration of the substance to be measured in the specimen is not appropriately measured in some cases.

The present invention has an object to provide a biosensor capable of making the operation at measurement easier while reducing the manufacturing cost.

One of aspects is a biosensor includes a plurality of electrodes including a working electrode, and a detection layer which is immobilized on the working electrode and contains a crosslinking agent, an electrically conductive macromolecule and an enzyme transferring and receiving electrons to and from the working electrode, wherein the working electrode is in an open system.

In the biosensor, a contact area of the detection layer with the working electrode may be defined by a predetermined area.

According to the present invention, it can provide a biosensor capable of making the operation at measurement easier and reducing the manufacturing cost.

DESCRIPTION OF EMBODIMENTS

Hereinafter, the enzyme electrodes according to the embodiments of the present invention will be described with reference to the drawings. The configurations of the embodiments described below are illustrative, and the present invention is not limited thereto.

First Embodiment

<Configuration of Biosensor>

Figure 1:
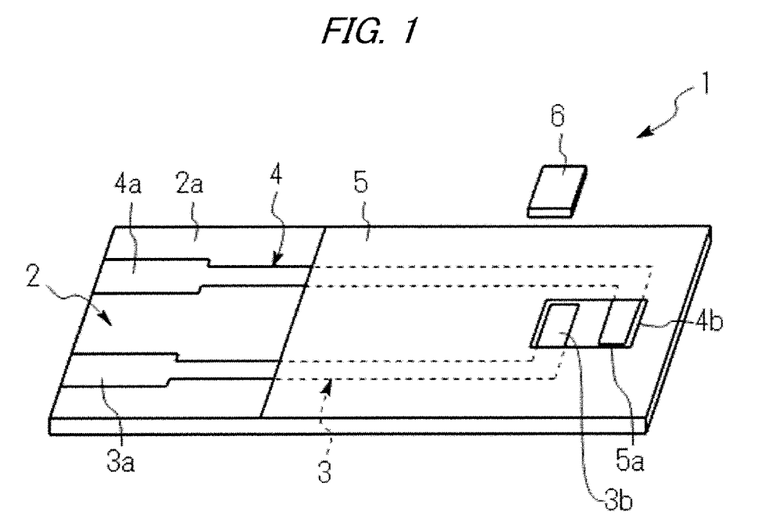
FIG. 1 is a drawing illustrating an example of the configuration of the biosensor according to an embodiment.

FIG. 1 is a drawing schematically illustrating an example of the configuration of the disposable biosensor according to the embodiment. In FIG. 1, the biosensor 1 includes an insulating base plate 2, electrodes 3, 4, an insulation layer 5 and a reagent layer (hereinafter referred to as "detection layer") 6. The biosensor 1 does not have a capillary formed with a spacer and a cover (a cover is not used in some cases). Specifically, at least the working electrode is in an open system.

<<Insulating Base Plate>>

The insulating base plate 2 is formed in the form of a rectangular flat plate having a longitudinal direction and a width direction. The insulating base plate 2 can be made of a thermoplastic resin such as polyetherimide (PEI), polyethylene terephthalate (PET) and polyethylene (PE), various resins (plastics) such as polyimide resins and epoxy resins, or insulating materials such as glasses, ceramics and papers.

<<Electrodes>>

The electrodes 3, 4 are formed on one surface 2a of the insulating base plate 2. The electrode 3 has one end part 3a and the other end part 3b, and the other end part 3b extends to the width direction of the insulating base plate 2 and is used as the working electrode. The one end part 3a is used as a lead unit (electrode extraction unit). The electrode 4 has one end part 4a and the other end part 4b, and the other end part 4b extends to the width direction of the insulating base plate 2 with a predetermined gap provided from the other end part 3b (working electrode) and is used as the counter electrode. The one end part 4a is also used as a lead unit (electrode extraction unit).

Each of the electrodes 3, 4 is formed using a metallic material such as gold (Au), platinum (Pt), silver (Ag) or palladium, or a carbon material such as carbon. For example, the electrodes 3, 4 can be formed as metal layers having a desired thickness by forming a film by depositing a metallic material by physical vapor deposition (PVD, e.g., sputtering) or chemical vapor deposition (CVD). Alternatively, the electrodes 3, 4 can be formed by screen printing an ink containing a carbon material on the insulating base plate 2. Alternatively, the electrodes 3, 4 can be formed as a silver/silver chloride electrode obtained by forming a film by screen printing. A three electrode system may also be used in which a reference electrode is the silver/silver chloride electrode, the carbon electrode obtained by forming a film using screen printing or the metal electrode obtained by forming a film using physical vapor deposition (PVD, e.g., sputtering) or chemical vapor deposition (CVD).

Various known materials are applicable to be the electrode material which forms the electrodes 3, 4 and the material for the insulating base plate 2. The size and thickness of the electrodes 3, 4 and the insulating base plate 2 can be determined as appropriate. The combination of the insulating base plate 2 and the electrodes 3, 4 is also called "base material". Note that, in the embodiment, a two electrode system including the working electrode and the counter electrode is presented as an example but a three electrode system further including a reference electrode may also be employed.

<<Insulation Layer>>

The insulation layer 5 is disposed on the base material, with an opening 5a formed to expose the other end parts 3b, 4b of the electrodes 3, 4. The one end parts 3a, 4a of the electrodes 3, 4 are similarly disposed so as to be exposed. The other end part 3b exposed at the opening 5a is used as the working electrode, and the other end part 4b is used as the counter electrode. Hereinafter, the other end part 3b may be denoted by "working electrode 3b" and the other end part 4b may be denoted by "counter electrode 4b".

The insulation layer 5 can also be formed by screen printing using a resist ink. Alternatively, the insulation layer 5 can also be formed by adhering a resin plate with the opening 5a formed thereon to the base material. Note that the insulation layer 5 is not disposed in some cases. The insulation layer 5 is to prevent a noise current from mixing in and the level difference at the opening 5a created by the insulation layer 5 is not to define a distribution (spreading) range of a sample to be adhered onto the electrodes (working electrode 3b, counter electrode 4b). Thus, the biosensor 1 does not have a capillary (a cover or a spacer) which covers the electrodes (working electrode 3b, counter electrode 4b).

<<Detection Layer>>

The detection layer 6 is immobilized on the working electrode 3b (the exposed other end part 3b). The detection layer 6 contains the enzyme which contacts the working electrode 3b, the electrically conductive macromolecule and a crosslinking agent, but does not contain an electron transfer mediator. The detection layer 6 may contain at least one of a sugar and the electrically conductive particle.

The object to be measured using the biosensor according to the embodiment is not an electric current which depends on the diffusion of a substance to be measured but a charge transfer limiting current based on the transfer of electrons from the substance to be measured to the electrode. This is an electric current generated when electrons from the enzyme are transferred to the electrode due to the reaction of the enzyme and the substance to be measured. The charge transfer limiting current is a time-independent steady-state current, and is preferably a steady-state current after the occurrence of the transient current due to the charging of an electric double layer.

For measuring the charge transfer limiting current, the working electrode is a "direct electron transfer-type enzyme electrode". The "direct electron transfer-type enzyme electrode" as used herein refers to a type of an enzyme electrode in which electrons are exchanged by the direct electron transfer between the enzyme and the electrode in such a way that electrons generated by an enzyme reaction in a reagent layer are directly, or mediated by the electrically conductive macromolecule, transferred to the electrode without the involvement of an oxidation reduction substance such as an electron transfer mediator.

Note that, even when an electron transfer mediator is used, the charge transfer limiting current can be measured in the case where the electron transfer mediator is immobilized so as not to be diffused.

The molecules of the enzyme within the detection layer 6 are crosslinked by the crosslinking agent and have a complicatedly interwined structure due to the electrically conductive macromolecule. The electrons generated by the enzyme reaction can be transferred to the electrode (working electrode 3b) directly or along the electrically conductive macromolecule having electrical conductivity. As described above, in the biosensor according to the embodiment, the electrons are exchanged between the enzyme and the working electrode 3b by the direct electron transfer in the detection layer 6.

Note that, in the physiological reaction system, the limiting distance within which the direct electron transfer occurs is considered from 1 to 2 nm. Even in the electron exchange in an electrochemical reaction system consisting of an electrode and an enzyme, the electron exchange on the electrode becomes difficult to detect in a longer distance than the above limiting distance unless the transfer of a mediator (e.g., transfer by diffusion) is involved. Consequently, within the detection layer 6, the active sites (the site at which electrons are generated by an enzyme reaction) of the enzyme and the electrically conductive sites of the electrically conductive macromolecule are located within a distance suitable for the electron transfer, specifically, the electrically conductive sites and the active sites are located close enough so that electrons are suitably transferred therebetween.

(Enzyme)

Examples of the enzyme include oxidoreductases. Examples of the oxidoreductase include glucose oxidase (GOD), galactose oxidase, bilirubin oxidase, pyruvic acid oxidase, D- or L-amino acid oxidase, amine oxidase, cholesterol oxidase, choline oxidase, xanthine oxidase, sarcosine oxidase, L-lactic acid oxidase, ascorbic acid oxidase, cytochrome oxidase, alcohol dehydrogenase, glutamate dehydrogenase, cholesterol dehydrogenase, aldehyde dehydrogenase, glucose dehydrogenase (GDH), fructose dehydrogenase, sorbitol dehydrogenase, lactate dehydrogenase, malate dehydrogenase, glycerol dehydrogenase, 17B hydroxysteroid dehydrogenase, estradiol 17B dehydrogenase, amino acid dehydrogenases, glyceraldehyde 3-phosphoric acid dehydrogenase, 3-hydroxysteroid dehydrogenase, diaphorase, cytochrome oxidoreductase, catalase, peroxidase, glutathione reductase and the like. Of these, oxidoreductases of sugars are preferable. Examples of the oxidoreductase of sugars include glucose oxidase (GOD), galactose oxidase, glucose dehydrogenase (GDH), fructose dehydrogenase and sorbitol dehydrogenase.

The oxidoreductase can further contain, as a catalytic subunit and a catalytic domain, at least one of pyrroloquinoline quinone (PQQ) and flavin adenine dinucleotide (FAD). Examples of the oxidoreductase containing PQQ include PQQ glucose dehydrogenase (PQQGDH). Examples of the oxidoreductase containing FAD include cytochrome glucose dehydrogenase (Cy-GDH) and glucose oxidase (GOD), which have an FAD-containing α-subunit.

The oxidoreductase can further contain an electron transfer subunit or an electron transfer domain. Examples of the electron transfer subunit include subunits, which have a heme with the function of electron exchange. Examples of the oxidoreductase containing such a heme-containing subunit include those containing cytochrome, and for example glucose dehydrogenase and a fusion protein of PQQGDH and cytochrome can be used.

Examples of the enzyme containing an electron transfer domain include cholesterol oxidase and quinoheme ethanol dehydrogenase (QHEDH (PQQ Ethanol dh)). For the electron transfer domain, it is further preferable to use domains containing cytochrome, which has a heme with the function of electron exchange. Examples include "QHGDH" (fusion enzyme; GDH with heme domain of QHGDH), sorbitol dehydrogenase (Sorbitol DH), D-fructose dehydrogenase (Fructose DH), *Agrobacterium tumefasience*-derived Glucose-3-Dehydrogenase (G3DH from *Agrobacterium tumefasience*) and cellobiose dehydrogenase. Note that the above fusion protein of PQQGDH and cytochrome, which is the example of the subunit containing cytochrome, and the cytochrome domain of PQQGDH, which is the example of the domain containing cytochrome, are disclosed in, for example, International Publication No. WO2005/030807.

Further, for the oxidoreductase, an oligomer enzyme composed of at least a catalytic subunit and a subunit containing cytochrome having a heme with the function of electron acceptor can be used.

An oxidoreductase which does not contain an electron transfer subunit may be used as the enzyme in the present embodiment. An example is cytochrome glucose dehydrogenase (Cy-GDH). Cy-GDH has an electron transfer subunit β, a catalytic subunit α and a catalytic subunit γ. In the present embodiment, Cy-GDH which does not have the electron transfer subunit β (contains the catalytic subunits α and γ) may be used as the enzyme.

Cy-GDH which does not have the electron transfer subunit β can be purchased at a lower price than Cy-GDH which has the electron transfer subunit β, the catalytic subunit α and the catalytic subunit γ. For this reason, when Cy-GDH which does not have the electron transfer subunit β is used as the enzyme to be contained in the detection layer 2, the manufacturing costs of the enzyme electrode can be reduced.

Cy-GDH which does not have the electron transfer subunit β further has higher stability as the substance than Cy-GDH which has the electron transfer subunit β, the catalytic subunit α and the catalytic subunit γ. This means that the enzyme electrode (biosensor) in which Cy-GDH not having the electron transfer subunit β is used can be stored for a longer period of time than the enzyme electrode (biosensor) in which Cy-GDH having the electron transfer subunit β, the catalytic subunit α and the catalytic subunit γ is used. Consequently, the type of enzyme electrode for a charge transfer limiting measurement, with a longer product life, can be obtained.

(Electrically Conductive Macromolecule (Conductive Polymer))

Examples of the electrically conductive polymer include polypyrrole, polyaniline, polystyrene sulfonate, polythiophene, polyisothianaphthene, polyethylene dioxythiophene (poly(3,4-ethylenedioxythiophene)poly(styrene sulfonate)), the combinations thereof and the like. Examples of the commercial products thereof include, as the polypyrrole, "SSPY" (ethyl 3-methyl-4-pyrrolecarboxylate) (manufactured by KAKENSANGYOU CORPORATION) and the like. Examples also include, as the polyaniline, "AquaPASS 01-x" (manufactured by TA Chemical Co., Ltd.) and the like. Examples further include, as the polystyrene sulfonate, "Poly-NaSS" (manufactured by TOSOH ORGANIC CHEMICAL CO., LTD.) and the like. Examples include, as the polythiophene, "ESPACER 100" (manufactured by TA Chemical Co., Ltd.) and the like. Examples include, as the polyisothianaphthene, "ESPACER 300" (manufactured by TA Chemical Co., Ltd.) and the like. Examples include, as the polyethylene dioxythiophene (poly(3,4-ethylenedioxythiophene)poly(styrene sulfonate)), "PEDOT-PSS" (Polyscience, Inc.) and the like.

Additionally, electrically conductive polymers with various properties (e.g., water solubility) can be used. Functional groups of the electrically conductive polymers preferably have a hydroxy group or a sulfo group.

(Sugar)

The detection layer 6 can contain the sugar, as illustrated in FIG. 1, in addition to the enzyme, the crosslinking agent and the electrically conductive macromolecule. The sugar is a sugar which does not serve as a substrate for the enzyme, and the number of constituent sugar of the sugar is, for example, 1 to 6, and preferably 2 to 6. These may be a D-form or an L-form, or a mixture thereof, and can be used singly or two or more thereof can be used in combination as appropriate. However, in the case where a sugar such as glucose is used as a measurement object, a sugar which is different from the sugar of the measurement object and which does not serve as a substrate for the enzyme is used as the sugar.

Examples of the disaccharide include xylobiose, agarobiose, carrabiose, maltose, isomaltose, sophorose, cellobiose, trehalose, neotrehalose, isotrehalose, inulobiose, vicianose, isoprimeverose, sambubiose, primeverose, solabiose, melibiose, lactose, lycobiose, epicellobiose, sucrose, turanose, maltulose, lactulose, epigentibiose, robinobiose, silanobiose, rutinose and the like. Examples of the trisaccharide include glucosyl trehalose, cellotriose, chacotriose, gentianose, isomaltotriose, isopanose, maltotriose, manninotriose, melezitose, panose, planteose, raffinose, soratriose, umbelliferose and the like.

Examples of tetrasaccharides include maltosyl trehalose, maltotetraose, stachyose and the like. Examples of the pentasaccharides include maltotriosyl trehalose, maltopentaose, verbascose and the like. Examples of the hexasaccharide include maltohexaose and the like.

(Crosslinking Agent)

Examples of the type of crosslinking agent include, specifically as the aldehyde group-containing compound, glutaraldehyde, formaldehyde, malonaldehyde, terephthalaldehyde, isobutyraldehyde, valeraldehyde, isovaleraldehyde, cinnamaldehyde, nicotinaldehyde, glyceraldehyde, glycoaldehyde, succinaldehyde, adipaldehyde, isophthalaldehyde, terephthalaldehyde and the like. Examples include, as the carbodiimide group-containing compound, hexamethylene diisocyanate, hydrogenated xylylene diisocyanate, xylylene diisocyanate, 2,2,4-trimethylhexamethylene diisocyanate, 1,12-diisocyanate dodecane, norbornane diisocyanate, 2,4-bis-(8-isocyanateoctyl)-1,3-dioctylcyclobutane, 4,4'-dicyclohexylmethane diisocyanate, tetramethylxylylene diisocyanate, isophorone diisocyanate and the like. The carbodiimide group-containing compounds are also commercially available under the names of CARBODILITE V-02, CARBODILITE V-02-L2, CARBODILITE V-04, CARBODILITE V-06, CARBODILITE E-01, CARBODILITE E-02, CARBODILITE V-01, CARBODILITE V-03, CARBODILITE V-05, CARBODILITE V-07, CARBODILITE V-09 (all are product names, manufactured by Nisshinbo Chemical Inc.) and the like.

Examples include, as the maleimide group-containing compound, m-maleimidobenzoyl-N-hydroxysuccinimide ester, sulfonsuccinimidyl 4-(p-maleimidophenyl)butyrate, m-maleimidobenzoyl sulfosuccinimide ester, N-γ-maleimidobutyryloxysuccinimide ester, succinimidyl 4-(N-maleidomethyl)cyclohexane 1-carboxylate, N-succinimidyl-2-maleimidoacetic acid, N-succinimidyl-4-maleimidobutyric acid, N-succinimidyl-6-maleimidohexanoic acid, N-succinimidyl-4-maleimidomethylcyclohexane-1-carboxylic acid, N-sulfosuccinimidyl-4-maleimidomethylcyclohexane-1-carboxylic acid, N-succinimidyl-4-maleimidomethylbenzoate, N-succinimidyl-3-maleimidobenzoate, N-succinimidyl-4-maleimidophenyl-4-butyric acid, N-sulfosuccinimidyl-4-maleimidophenyl-4-butyric acid, N,N'-oxydimethylene-dimaleimide, N,N'-o-phenylene-dimaleimide, N,N'-m-phenylene-dimaleimide, N,N'-p-phenylene-dimaleimide, N,N'-hexamethylene-dimaleimide, N-succinimidyl maleimide carboxylate and the like. Examples also include commercial products such as SANFEL BM-G (manufactured by SANSHIN CHEMICAL INDUSTRY CO., LTD.) and the like.

Examples include, as the oxazoline group-containing compound, oxazoline compounds such as 2,2'-bis-(2-oxazoline), 2,2'-methylene-bis-(2-oxazoline), 2,2'-ethylene-bis-(2-oxazoline), 2,2'-trimethylene-bis-(2-oxazoline), 2,2'-tetramethylene-bis-(2-oxazoline), 2,2'-hexamethylene-bis-(2-oxazoline), 2,2'-octamethylene-bis-(2-oxazoline), 2,2'-ethylene-bis-(4,4'-dimethyl-2-oxazoline), 2,2'-p-phenylene-bis-(2-oxazoline), 2,2'-m-phenylene-bis-(2-oxazoline), 2,2'-m-phenylene-bis-(4,4'-dimethyl-2-oxazoline), bis-(2-oxazolinylcyclohexane)sulfide, bis-(2-oxazolinylnorbornane)sulfide and the like.

Examples include, as the addition polymerizable oxazoline compound, 2-vinyl-2-oxazoline, 2-vinyl-4-methyl-2-oxazoline, 2-vinyl-5-methyl-2-oxazoline, 2-isopropenyl-2-oxazoline, 2-isopropenyl-4-methyl-2-oxazoline, 2-isopropenyl-5-ethyl-2-oxazoline and the like, and polymerized or copolymerized compounds of one or more thereof can be used.

The oxazoline group-containing compounds are also commercially available under the names of EPOCROS WS-500, EPOCROS WS-700, EPOCROS K-1010E, EPOCROS K-1020E, EPOCROS K-1030E, EPOCROS K-2010E, EPOCROS K-2020E, EPOCROS K-2030E, EPOCROS RPS-1005, EPOCROS RAS-1005 (all manufactured by NIPPON SHOKUBAI CO., LTD.), NK Linker FX (manufactured by Shin-Nakamura Chemical Co., Ltd.) and the like.

Examples specifically include, as the epoxy group-containing compound, sorbitol polyglycidyl ether, polyglycerol polyglycidyl ether, diglycerol polyglycidyl ether, glycerol polyglycidyl ether, trimethylolpropane polyglycidyl ether, ethylene glycol diglycidyl ether, polyethylene glycol diglycidyl ether, propylene glycol diglycidyl ether, polypropylene glycol diglycidyl ether and the like, and two or more of these compounds can also be used in combination. The epoxy group-containing compounds are also commercially available under the names of Denacol EX-611, Denacol EX-612, Denacol EX-614, Denacol EX-614B, Denacol EX-512, Denacol EX-521, Denacol EX-421, Denacol EX-313, Denacol EX-314, Denacol EX-321, Denacol EX-810, Denacol EX-811, Denacol EX-850, Denacol EX-851, Denacol EX-821, Denacol EX-830, Denacol EX-832, Denacol EX-841, Denacol EX-861, Denacol EX-911, Denacol EX-941, Denacol EX-920, Denacol EX-145 and Denacol EX-171 (all are product names, manufactured by Nagase ChemteX Corporation), SR-PG, SR-2EG, SR-8EG, SR-8EGS, SR-GLG, SR-DGE, SR-4GL, SR-4GLS and SR-SEP (all are product names, manufactured by Sakamoto Yakuhin Kogyo Co., Ltd.), Epolite 200E, Epolite 400E, Epolite 400P (all are manufactured by KYOEISHA CHEMICAL Co., LTD.) and the like.

The type of crosslinking agent is not limited to the above compounds and commercial products but may be any compounds containing at least one functional group of an aldehyde group, a maleimide group, a carbodiimide group, an oxazoline group and an epoxy group. The form of crosslinking agent is not limited and may be in the form of a monomer or a polymer.

(Electrically Conductive Particles)

The detection layer 6 can further contain electrically conductive particles. For the electrically conductive particles, metal particles such as gold, platinum, silver or palladium, or higher-order structures made of a carbon material, can be used. The higher-order structure can contain, for example, electrically conductive carbon black, carbon nanotube (CNT) and carbon particles or carbon fine particles such as fullerene. Examples of the electrically conductive carbon black include Ketjenblack (manufactured by Degussa AG), BLACK PEARL (Cabot Corporation) and the like.

Note that the surface of the detection layer 6 may also be covered with an outer layer film such as cellulose acetate. Examples of the raw material for the outer layer film include, among others, polyurethane, polycarbonate, polymethylmethacrylate, butylmethacrylate, polypropylene, polyether ether ketone and the like.

(Method for Manufacturing Biosensor)

The above biosensor 1 is, for example, produced (manufactured) as follows. Specifically, metal layers which function as the electrodes 3, 4 are formed on one surface 2a of the insulating base plate 2. For example, a film is formed on one surface 2a of the insulating base plate 2 in the shape of film having a predetermined thickness (e.g., about 100 μm) by depositing a metallic material by physical vapor deposition (PVD, e.g., sputtering) or chemical vapor deposition (CVD). Thus, the metal layers (electrodes 3, 4) having a desired thickness (e.g., about 30 nm) are formed. Instead of the metal layer, the electrodes 3, 4 can alternatively be formed, for example, by screen printing a carbon material.

Next, the insulation layer 5 having a predetermined exposure pattern (having the opening 5a) is formed by screen printing using a resist ink on one surface 2a on which the electrodes 3, 4 are formed.

Next, the detection layer 6 is formed on the working electrode 3b. For example, a solution (reagent) containing at least the enzyme, the electrically conductive macromolecule and the crosslinking agent is prepared. When a sugar is added to the reagent, the concentration of the sugar is preferably from 0.1 to 2 wt %, and more preferably 0.2 to 2 wt %. The solution (reagent) is dropped onto the surface of the working electrode 3b. The detection layer 6 is formed on the working electrode 3b when the solution (reagent) is solidified by drying on the working electrode 3b. Thus, the biosensor 1 wherein the working electrode 3b is in an open system can be obtained.

The use of the biosensor 1 according to the embodiment enables the concentration measurement of a substance to be measured in a sample (specimen) based on a charge transfer limiting current. The substance to be measured as referred herein is not particularly limited as long as the substance is measurable by the measurement method using the biosensor 1, but is preferably a substance of a biological origin and can be an indicator of a disease or health conditions. Examples of the substance include glucose, cholesterol and the like. The sample is not particularly limited as long as it contains a substance to be measured. A biological sample is preferable. Examples of the biological sample include blood, urine and the like.

(Measuring Apparatus)

Figure 2:
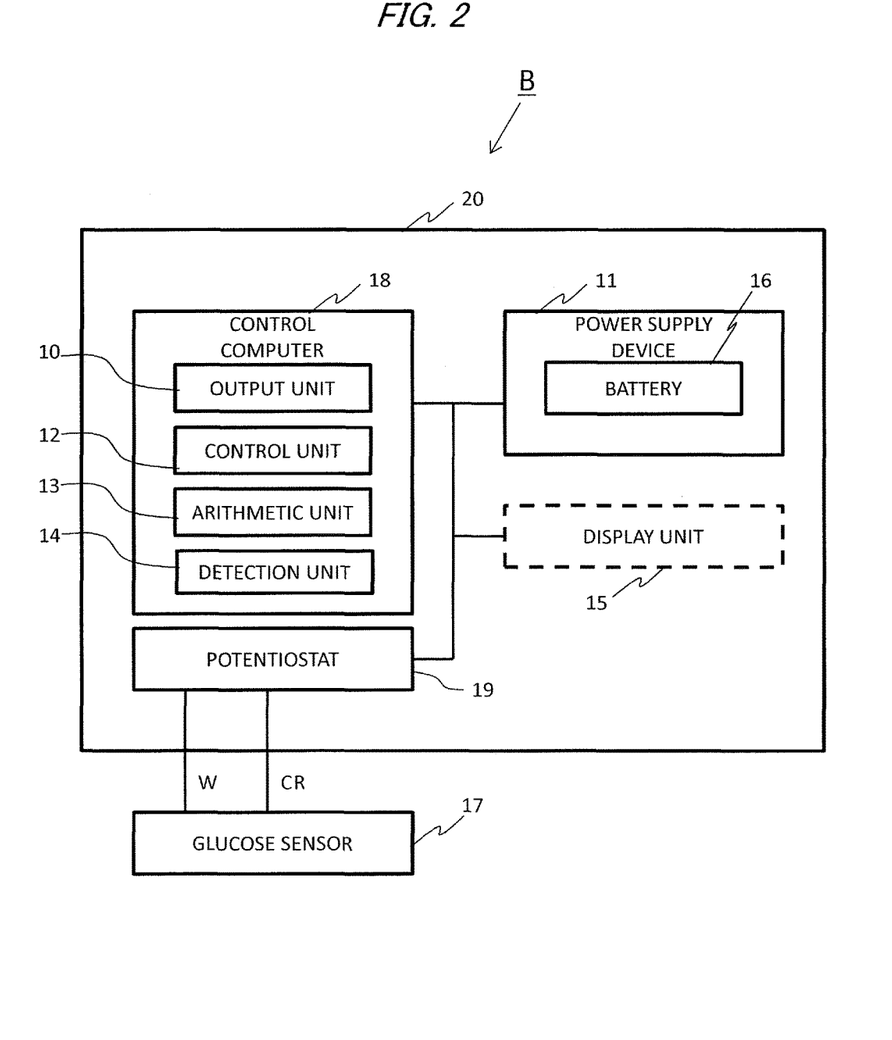
FIG. 2 is a drawing illustrating an example of the configuration of a measuring apparatus.

Next, the measuring apparatus for measuring a concentration of the substance using the biosensor 1 according to the embodiment is described. A glucose measuring apparatus which uses a glucose sensor, which is an example of the biosensor 1, is illustrated here. However, the measuring apparatus is not limited to the glucose measuring apparatus, and the purpose of use of the measuring apparatus changes depending on the substance to be measured by the biosensor 1.

FIG. 2 illustrates an example of the configuration of main electronic components housed in the measuring apparatus B. A control computer 18, a potentiostat 19 and a power supply device 11 are provided on a base plate 20 housed in a housing. The control computer 18 includes, as hardware, a processor such as CPU (Central Processing Unit), recording media such as memories (RAM (Random Access Memory) and ROM (Read Only Memory)) and the communication unit.

When the processor loads a program stored in the recording medium (e.g., ROM) to the RAM and executes the program, the control computer 18 functions as an apparatus including an output unit 10, a control unit 12, an arithmetic unit 13 and a detection unit 14. The control computer 18 may also include an auxiliary memory such as a semiconductor memory (EEPROM or flash memory) or a hard disk for storing programs and data.

The control unit 12 controls the timing for applying the voltage, the value of the voltage to be applied and the like. The power supply device 11 includes a battery 16, and supplies electricity to the control computer 18 and the potentiostat 19 for operation. It is also possible to dispose the power supply device 11 outside the housing.

The potentiostat 19 is a device which maintains the potential of the working electrode constant with respect to the reference electrode and is controlled by the control unit 12. The potentiostat 19 applies a predetermined amount of voltage between the counter electrode and the working electrode of the glucose sensor 17 using terminals CR, W, measures the response electric current of the working electrode which can be obtained at the terminal W, and sends the measurement results of the response electric current to the detection unit 14.

The arithmetic unit 13 calculates and stores the concentration of the substance to be measured based on the value of the detected electric current. The output unit 10 carries out data communication with the display unit 15 and sends the calculated result of the concentration of the substance to be measured, which is provided by the arithmetic unit 13, to the display unit 15. The display unit 15 is capable of displaying, for example, the calculated result of the glucose concentration received from the measuring apparatus B, on a display screen in a predetermined format.

Figure 3:
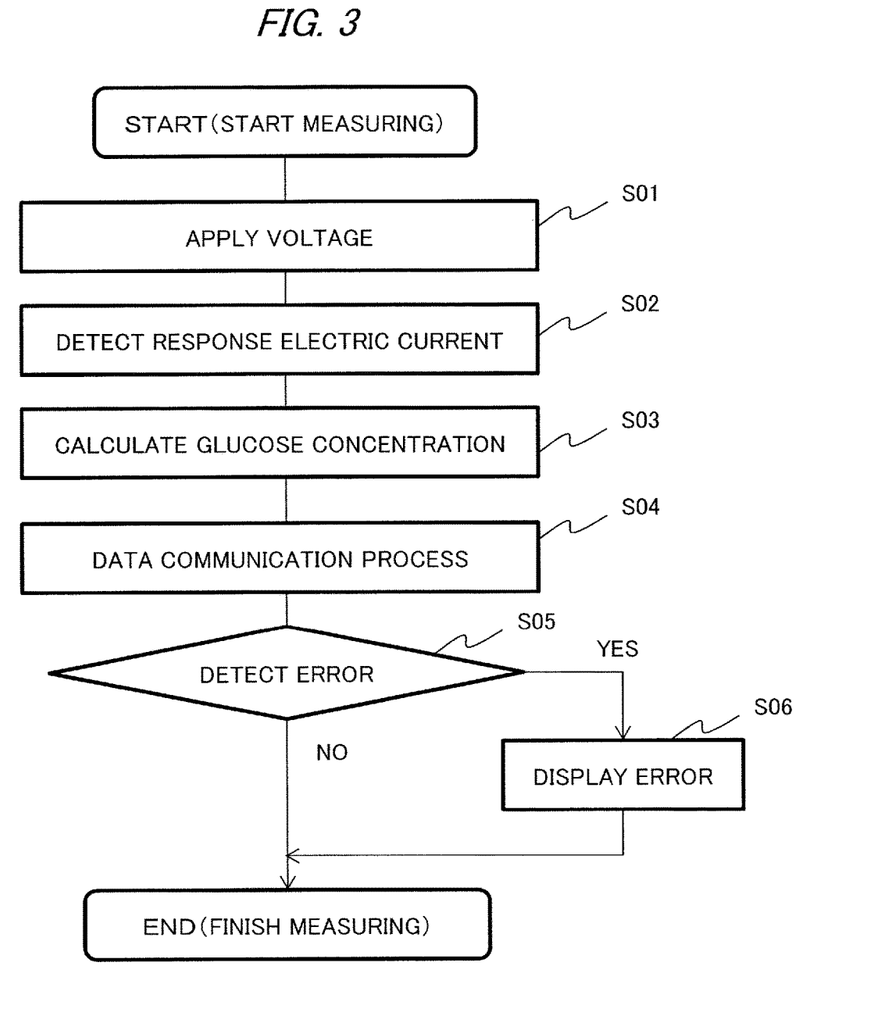
FIG. 3 is a flow chart illustrating an example of the processing sequence carried out by the measuring apparatus.

FIG. 3 is a flow chart illustrating an example of the processing sequence of the glucose concentration measurement carried out by the control computer 18. The CPU (control unit 12) of the control computer 18 receives an instruction to start the measurement of the glucose concentration. The control unit 12 controls the potentiostat 19 to apply a predetermined amount of voltage to the working electrode, and starts measuring the response electric current from the working electrode (Step S01). Note that the detection of the installation of the glucose sensor 17 to the measuring apparatus B may be used as the instruction to start the concentration measurement.

Next, the potentiostat 19 measures the response electric current generated by the application of voltage, specifically, the charge transfer limiting current based on the transfer to the electrode of electrons derived from the substance to be measured (glucose, herein) in the sample, and sends the measured current to the detection unit 14 (Step S02). As the charge transfer limiting current, the steady-state current after the occurrence of the transient current due to the charging of an electric double layer, for example, 1 to 20 seconds after the application of voltage, is measured.

The arithmetic unit 13 carried out arithmetic processing based on the electric current value and calculates the glucose concentration (Step S03). For example, the formulae for calculating the glucose concentration or the data of the calibration curve of the glucose concentration, which correspond to an enzyme (e.g., glucose dehydrogenase) contained in the detection layer disposed on the working electrode, are preinstalled to the arithmetic unit 13 in the control computer 18. The arithmetic unit 13 calculates the glucose concentration using these calculation formulae or the calibration curve.

The output unit 10 sends the calculated result of the glucose concentration to the display unit 15, through a communication link provided with the display unit 15 (Step S04). Thereafter, the control unit 12 determines if there are any measurement errors detected (Step S05), completes the measurement if there is no error and displays the glucose concentration on the display unit. If there are any errors, a notification of error is displayed, and then the flow sequence illustrated in FIG. 3 is completed. The calculation result may be stored in a storage medium and read out the calculation result from the storage medium to display and confirm. Note that the detection of measurement error by the control unit 12 (Step S05) is carried out after the calculated result is sent to the display unit 15 (Step S04) in the example of FIG. 3, but it is also possible to carry out these steps in switching orders.

EXAMPLE

Hereinafter, Examples of the enzyme electrode are described.

<Test 1>

A plurality of biosensors having capillaries with different spacer thicknesses were produced and glucose was measured.

(Production of Biosensor)

A working electrode and a counter electrode were formed on one surface of an insulating base plate by screen printing using a carbon ink, and a reference electrode was formed by screen printing using Ag/AgCl to form an electrode system consisting of three electrodes. The reagent solution prepared with the following formulation was dropped onto the working electrode and solidified by drying to form a detection layer. Further, a capillary was formed, using a spacer and a cover, on the insulating base plate on which the electrode system was formed to obtain biosensors with spacer thicknesses of 150 μm, 300 μm and 450 μm, respectively.
[Formulation of Reagent]
　Phosphate buffer solution: (pH 5.8): 10 mM
　Sucrose: 0.5%
　Enzyme (Cy-GDH: γαβ): 4.5 mg/mL
　Electrically conductive macromolecule: sulfonated polyaniline aqueous solution (tradename: aquaPASS-01x, manufactured by Mitsubishi Rayon Co., Ltd.): 0.4%
　Oxazoline group-containing polymer EPOCROS WS-700 (NIPPON SHOKUBAI CO., LTD.): 6.0%
　Lion Paste W-311N (manufactured by Lion Corporation): 2.42% Note that "%" represents the wt % concentration of the reagent contained in the reagent solution.
(Sample)
20 mM HEPES solutions (pH 7.0), having glucose concentrations in samples of 0, 100 mg/dL, 200 mg/dL, 400 mg/dL and 800 mg/dL, respectively, were prepared as specimens (samples). Glucose concentrations were measured using each of the biosensors by the chronoamperometry method (+60 mV vs. Ag/AgCl) under an atmosphere at 23±1° C.

Figure 4:
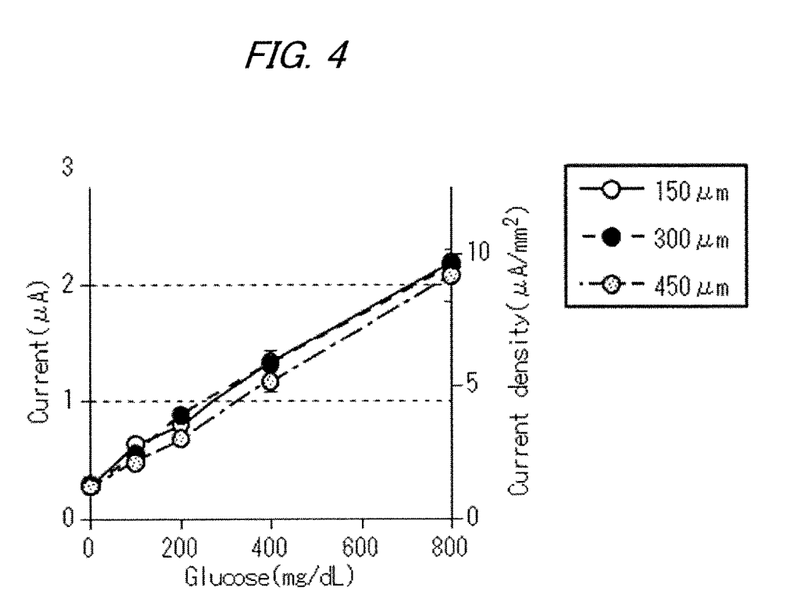
FIG. 4 is a graph depicting the calibration curves based on the results of Test 1, the measurement results of glucose concentrations using a chronoamperometry method.

FIG. 4 is a graph depicting the results of Test 1, the calibration curves based on the measurement results of glucose concentrations using the chronoamperometry method. According to the results of FIG. 4, the calibration curves having similar slopes were obtained in a spacer thickness-independent manner. This means that the amount of a sample adhered to the electrode does not affect the response electric current value.

<Test 2>

Next, biosensors with a capillary and biosensors without a capillary were produced as the biosensors having a detection layer containing an electron transfer mediator, and the measurement was carried out by the chronoamperometry method.
(Formulation of Reagent)
　Enzyme (FAD-GDH): 1 U
　Mediator (Ru complex, 1-methoxy-PMS): 200 mM
　ACES buffer solution: (pH 7.5): 0.17 mM
　Smectite (Lucentite SWN): 0.2%
(Sample)
Whole bloods having glucose concentrations in samples of 100 mg/dL, 321 mg/dL and 624 mg/dL, respectively, were prepared as specimens (samples). Glucose response electric currents were measured using each of the biosensors by the chronoamperometry method (+200 mV vs. Ag/AgCl) under an atmosphere at 24±1° C.

Figure 5:
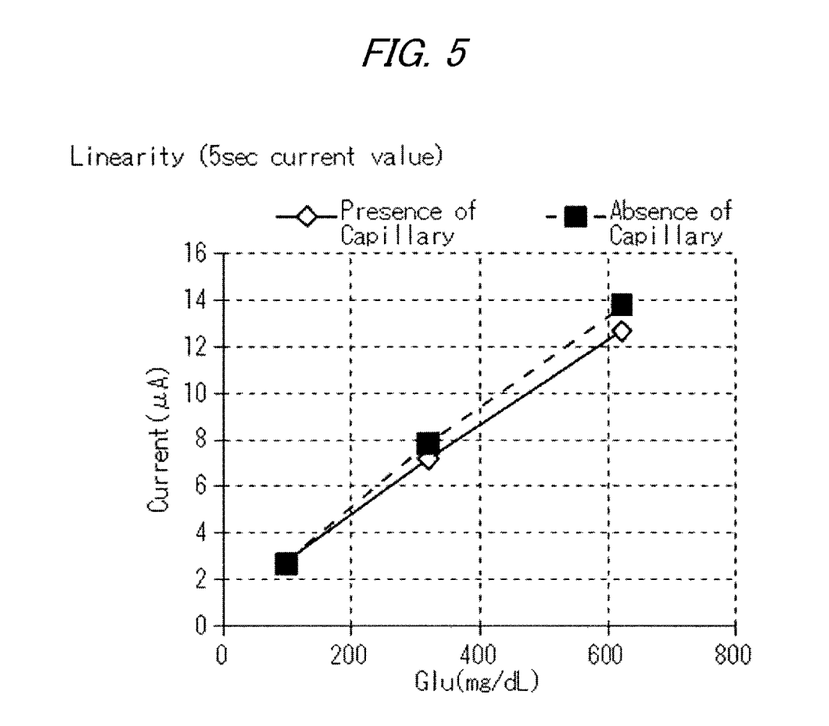
FIG. 5 is a graph depicting the calibration curves based on the results of Test 2, specifically, the measurement results of glucose concentrations by a chronoamperometry method.

FIG. 5 is a graph depicting the results of Test 2, specifically the calibration curves based on the measurement results of glucose concentrations by the chronoamperometry method. As revealed in FIG. 5, the cases without a capillary have higher response electric current values than the cases with a capillary, whereby the response electric current value is verified to have been affected by the absence of capillary.

<Test 3>

Example 1

Next, the biosensor according to Example 1 was produced as follows. On one surface 2a of the insulating base plate 2, two electrodes were formed consisting of the working electrode 3b formed by screen printing using a carbon ink and the counter electrode 4b formed by screen printing using a silver/silver chloride ink (Ercon Inc.). No capillary was provided on the electrodes to leave the working electrode 3b and the counter electrode 4b in an open system.

The reagent ink prepared with the following formulation was screen printed on the working electrode 3b and solidified by drying to form the detection layer 6.
[Formulation]
　Phosphate buffer solution: (pH 5.8): 10 mM
　Sucrose: 0.5%
　GDH: 7 mg/mL
　Electrically conductive macromolecule: sulfonated polyaniline aqueous solution (tradename: aquaPASS-01x, manufactured by Mitsubishi Rayon Co., Ltd.): 0.40%
　Oxazoline group-containing polymer EPOCROS WS-700 (NIPPON SHOKUBAI CO., LTD.): 5.0%
　Ketjenblack: 0.8%
Note that "%" represents the wt % concentration of the reagent contained in the reagent solution.

Whole bloods having glucose concentrations of 0 (Blank: B) and 336 mg/dL (Sample: S) were used as specimens (samples). Each of the samples was dispensed (spotted) on the electrode of each biosensor and glucose concentrations were measured by the chronoamperometry method under an atmosphere at 25° C. The concentration measurement was carried out by preparing a plurality of the above biosensors with different amounts of spotted samples in 1 μL, 2 μL and 4 μL.

Figure 6:
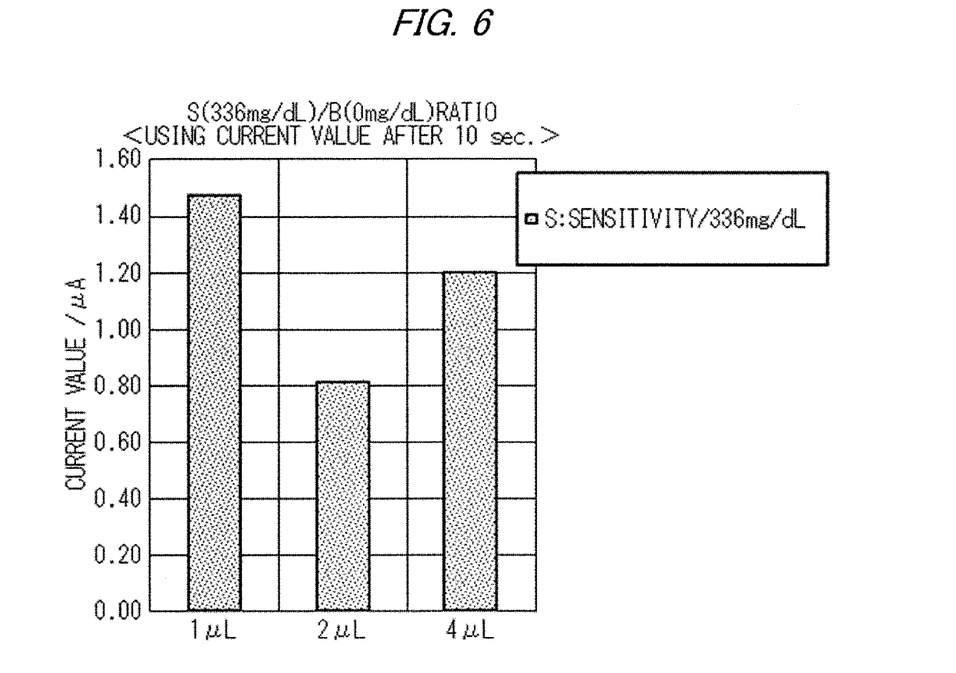
FIG. 6 is a graph depicting S/B (Sample/Blank) ratios based on the measurement results of glucose concentrations carried out using the biosensor of Example 1.

FIG. 6 is a graph depicting S/B (Sample/Blank) ratios based on the measurement results of glucose concentrations carried out using the biosensor of Example 1. As revealed in FIG. 6, the S/B ratios had S/B ratio levels of about 20 in all of 1 μL, 2 μL and 4 μL, whereby no dependency on the specimen amount was suggested.

<Test 4>

Comparative Example 1

The biosensors of Example 1 with a capillary were prepared as Comparative Example 1. The biosensors each having a capillary height of 10 μm, 30 μm, 50 μm, 100 μm, 200 μm were produced. The formulation of the detection layer 6 was the same as Example 1. Using aqueous solutions of 0 and 300 mg/dL as specimens (samples), the electrode was immersed in the sample to allow the specimen to contact the electrode.

Figure 7:
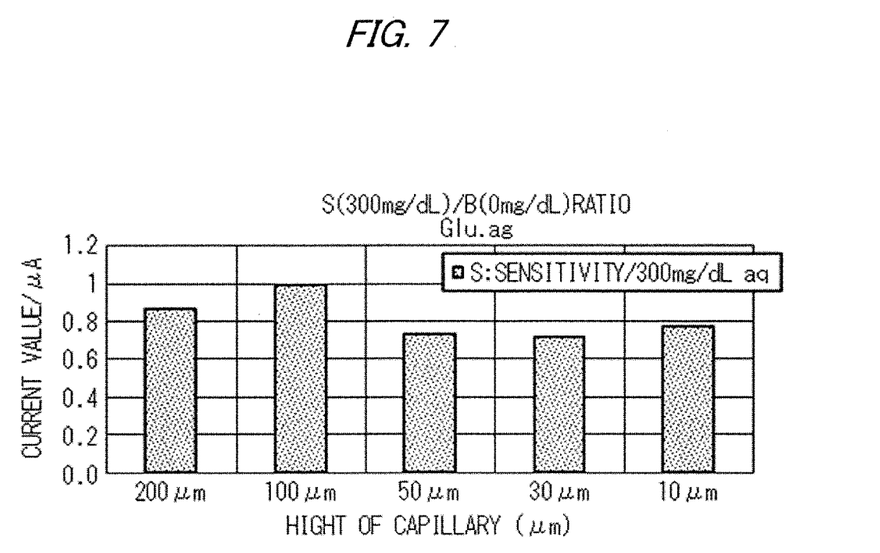
FIG. 7 is a graph depicting S/B ratios based on the measurement results by the CV method and the CA method carried out using the biosensor of Comparative Example 1.

The biosensors according to Comparative Example 1 were examined for the electrode response properties using the cyclic voltammetry method (CV method) and the chronoamperometry method (CA method) under an atmosphere at 25° C. FIG. 7 is a graph depicting S/B ratios based on the measurement results by the CV method and the CA method carried out using the biosensor of Comparative Example 1. As revealed in FIG. 7, it was verified that the S/B ratio is not dependent on the height of a capillary.

According to Test 1 to Test 4, it was verified that the response electric current value does not depend on the specimen amount or the height of a capillary. Thus, according to the biosensor 1 wherein at least the working electrode is in an open system, highly accurate concentration measurement can be achieved without adjusting or controlling a specimen amount by a capillary. Consequently, the absence of a capillary can reduce the manufacturing costs of the biosensor due to the decreased number of components. Further, differences in measurement results caused by the way a user of the biosensor 1 handles the biosensor 1 can be obviated due to the independency on the specimen amount. Specifically, the biosensor can be easily handled by a user. Note that the biosensor according to the embodiment does not need to cover the electrode with a capillary (an open system), because of which a configuration wherein a lancet is provided with the biosensor to enable a specimen to be spotted on the electrode in conjunction with the puncture can be applicable.

Second Embodiment

Hereinafter, the second embodiment is described. The second embodiment has the same configuration as in the first embodiment, and hence the different aspects are mainly described but the descriptions of the common aspects are omitted.

The charge transfer limiting current described in the first embodiment is represented by the following formula (1). The formula (1) reveals that the electric current is proportional to the concentration of the substrate and to the enzyme reaction rate constant. When the constant term is defined as X, the formula (1) can be expanded to a formula (2). Note that the constant term X may include a correction coefficient and the like, although not appeared in the formulae (1) and (2).

[formula (1)]

$$i = \frac{nFAC_s^0 K_{cat} \tau_E}{Km} \quad (1)$$

[formula (2)]

$$i = X * \frac{K_{cat}}{Km} * C_s^0 \quad (2)$$

i: current(A),
n: the number of reaction electrons(eq/mol),
F: Faraday constant(96.485 C./eq),
A: electrode area(cm²),
$C_s^0$: consentration(mol/cm³) of substrate(S),
$\tau_E$: oxygen content(mol),
$K_{cat}/K_m$: oxygen reaction rate constant The formula (1) is derived, taking the initial rate formula of the enzyme reaction and the formula of the electron transfer rate from the enzyme to the electrode into the consideration, by expanding the formulae where the values of these formulae are equal. The biosensor according to the first embodiment measures, for example, a concentration of a substance to be measured (substrate) using the above formulae (1) and (2).

The formula (1) is a formula of charge transfer limiting current, which does not include the diffusion coefficient included in the Cottrell current of the initial rate formula of the enzyme reaction. As revealed in the formula (1), the electric current is proportional to the enzyme reaction rate constant. In the measurement method of a substance to be measured according to the first embodiment, electrons are transferred to the electrode without being mediated by an oxidation reduction reaction by a mediator such as an electron acceptor substance. For this reason, it is revealed that the charge transfer limiting current is not affected by the diffusion of the substance or does not depend on time.

Note that the electrode system can be confirmed to be the charge transfer limiting by examining the presence or absence of a peak and the pattern of electric current increase due to the sweep direction of the voltage using cyclic voltammetry or the like.

Figure 8:
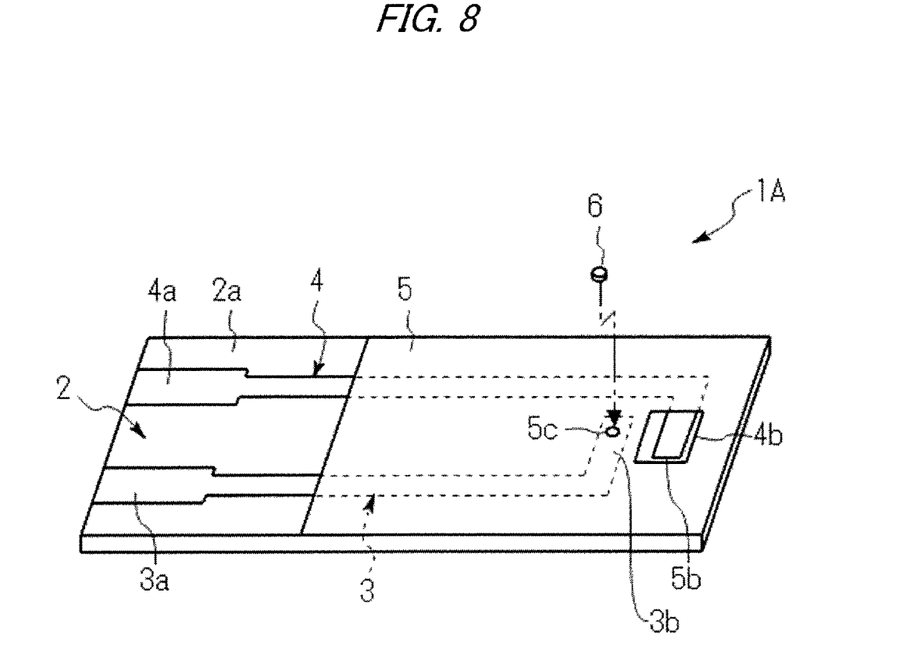
FIG. 8 is a drawing illustrating an example of the configuration of the biosensor according to the second embodiment.

The biosensor according to the second embodiment also includes a "direct electron transfer-type enzyme electrode" for measuring the charge transfer limiting current. Further, the biosensor according to the second embodiment, the detection layer wherein a contact area with the working electrode is defined by a predetermined area is formed on the working electrode. Specifically, the contact area of the detection layer with the working electrode is defined by a predetermined area. The contact area of the detection layer with the working electrode can be defined by applying (painting) a detection layer material to the working electrode among a plurality of electrodes, but not simply dropping a liquid detection layer material. With this procedure, the "A: electrode surface area" and "n: reaction electron number" in the formula (1) can be defined. Thus, inconsistencies of the response electric currents between individual biosensors are reduced and the simultaneous repeatability can be improved.

For defining the contact area of the detection layer with the working electrode, the formation of an insulation layer on the insulating base plate on which the electrodes are formed can be presented as an example. The insulation layer is formed so that the working electrode is exposed at the bottom surface thereof and has an opening which is filled with the detection layer material. The opening has a connected inner wall surface to regulate, within the opening, the diffusion range of the detection layer material with which the opening is filled. When the detection layer material with which the opening is filled is solidified by drying, the detection layer with which the opening is filled (burying the opening) is formed. The bottom area of the opening has a size defined to match the contact area of the detection layer with the working electrode, and the opening is filed with the detection layer material in at least an amount of sufficiently burying the bottom of the opening. With this procedure, the detection layer wherein the contact area with the working electrode is defined to be a predetermined area (contacting the working electrode in a predetermined area) can be easily formed on the working electrode. The insulation layer can be formed by screen printing using a nonconductive ink (also called a resist ink). The insulation layer can also be formed, in addition to the screen printing, by processes using various resists such as photoresists and insulating tapes or the like as long as the opening capable of defining the contact area of the working electrode with the detection layer can be formed.

As another usage, the contact area of the detection layer with the working electrode can be determined corresponding to the reaction rate of an enzyme. The reaction rate of an enzyme may vary by lots with different specific activities. For this reason, the areas of the detection layer and working electrode corresponding to the reaction rate of an enzyme are determined in advance by experiments or the like, and the detection layer is formed over the contact area corresponding to the reaction rate of the enzyme by each lot. With this procedure, the inconsistencies on the simultaneous repeatability by lots can be reduced.

FIG. 8 is a drawing illustrating an example of the configuration of the biosensor 1A according to the second embodiment. The biosensor 1A has a different configuration in the following aspects from the biosensor 1 (FIG. 1) of the first embodiment.

The insulation layer 5 has, in place of the opening 5a (FIG. 1), an opening 5b and an opening 5c. The opening 5b is formed so that the counter electrode 4b and the upper surface of the insulating base plate 2 surrounding therearound are exposed.

On the other hand, the opening 5c is formed on the working electrode 3b, and the working electrode 3b is covered with the insulation layer 5 except the part which is exposed at the opening 5c. The opening 5c has a predetermined bottom area and a connected inner wall surface. In the example illustrated in FIG. 8, the opening 5c has a circular planar shape and a connected inner wall surface having a cylindrical side surface shape.

The size (bottom area) of the opening 5c is formed on the working electrode 3b so as to match the contact area of the detection layer 6, which contacts the working electrode 3b. The detection layer 6 is formed when the opening 5c is adequately filled with the detection layer material. In the example of FIG. 8, the detection layer 6 is in the cylindrical shape to bury the opening 5c.

As described above, when the detection layer 6 is formed using the opening 5c having the defined bottom area, the contact area of the working electrode 3b with the detection layer 6 is defined. The component elements of the detection layer 6 are as described in the first embodiment.

Note that, in the example of FIG. 8, the planar shape of the opening 5c is circular and the inner wall surface is the cylindrical side surface. However, the opening 5c may be formed in the shape of a taper with the inner wall surface being a truncated cone side surface. The planar shape of the opening 5c and the shape of the inner wall surface can be determined as appropriate as long as the connected inner wall surface, which regulates the diffusion range of the detection layer material with which the opening is filled, can be formed. For example, the planar shape of the opening 5c may be elliptical, triangle, quadrangle or polygon that consists of five or more sides. Additionally, the shape of the inner wall surface of the opening 5c may be a pillar side surface corresponding to the planar shape or a pillar side surface not corresponding to the planar shape. Specifically, the shape of the opening 5c can be determined as appropriate as long as the contact area of the detection layer 6 with the working electrode 3b can be defined to be a predetermined area.

According to the biosensor of the second embodiment as described above, the working electrode being in an open system (a capillary is absent) makes the spotting of a sample easier. Further, the detection layer 6 contacts the working electrode 3b in a predetermined area, specifically, the contact area of the detection layer 6 with the working electrode 3b is defined. In this way, the CV value (simultaneous repeatability) can be improved. Specifically, errors between biosensors are reduced and the accuracy can be stabilized.

What is claimed is:
1. A biosensor comprising:
  a plurality of electrodes including a working electrode, and
  an immobilized detection layer painted onto the working electrode and containing a crosslinking agent, an electrically conductive macromolecule and an enzyme, where the enzyme is capable of transferring and receiving electrons to and from the working electrode,
  wherein:
    the working electrode is in an open system,
    the enzyme contains a catalytic subunit, a catalytic domain and an electron transfer subunit or an electron transfer domain, and
    contact area between the painted detection layer and the working electrode is defined by a predetermined area.
2. The biosensor according to claim 1, wherein the crosslinking agent comprises at least one selected from the group consisting of an aldehyde group-containing compound, a carbodiimide group-containing compound, a maleimide group-containing compound, an oxazoline group-containing compound, and an epoxy group-containing compound.
3. The biosensor according to claim 1, wherein the crosslinking agent comprises at least one selected from the group consisting of glutaraldehyde, formaldehyde, malonaldehyde, terephthalaldehyde, isobutyraldehyde, valeraldehyde, isovaleraldehyde, cinnamaldehyde, nicotinaldehyde, glyceraldehyde, glycoaldehyde, succinaldehyde, adipaldehyde, isophthalaldehyde, and terephthalaldehyde.
4. The biosensor according to claim 1, wherein the crosslinking agent comprises at least one selected from the group consisting of hexamethylene diisocyanate, hydrogenated xylylene diisocyanate, xylylene diisocyanate, 2,2,4-trimethylhexamethylene diisocyanate, 1,12-diisocyanate dodecane, norbornane diisocyanate, 2,4-bis-(8-isocyanateoctyl)-1,3-dioctylcyclobutane, 4,4'-dicyclohexylmethane diisocyanate, tetramethylxylylene diisocyanate, and isophorone diisocyanate.
5. The biosensor according to claim 1, wherein the crosslinking agent comprises at least one selected from the group consisting of m-maleimidobenzoyl-N-hydroxysuccinimide ester, sulfonsuccinimidyl 4-(p-maleimidophenyl)butyrate, m-maleimidobenzoyl sulfosuccinimide ester, N-γ-maleimidobutyryloxysuccinimide ester, succinimidyl 4-(N-maleidomethyl)cyclohexane 1-carboxylate, N-succinimidyl-2-maleimidoacetic acid, N-succinimidyl-4-maleimidobutyric acid, N-succinimidyl-6-maleimidohexanoic acid, N-succinimidyl-4-maleimidomethylcyclohexane-1-carboxylic acid, N-sulfosuccinimidyl-4-maleimidomethylcyclohexane-1-carboxylic acid, N-succinimidyl-4-maleimidomethylbenzoate, N-succinimidyl-3-maleimidobenzoate, N-succinimidyl-4-maleimidophenyl-4-butyric acid, N-sulfosuccinimidyl-4-maleimidophenyl-4-butyric acid, N,N'-oxydimethylene-dimaleimide, N,N'-o-phenylene-dimaleimide, N,N'-m-phenylene-dimaleimide, N,N'-p-phenylene-dimaleimide, N,N'-hexamethylene-dimaleimide, and N-succinimidyl maleimide carboxylate.
6. The biosensor according to claim 1, wherein the crosslinking agent comprises at least one selected from the group consisting of 2,2'-bis-(2-oxazoline), 2,2'-methylene-bis-(2-oxazoline), 2,2'-ethylene-bis-(2-oxazoline), 2,2'-trimethylene-bis-(2-oxazoline), 2,2'-tetramethylene-bis-(2-oxazoline), 2,2'-hexamethylene-bis-(2-oxazoline), 2,2'-octamethylene-bis-(2-oxazoline), 2,2'-ethylene-bis-(4,4'-dimethyl-2-oxazoline), 2,2'-p-phenylene-bis-(2-oxazoline), 2,2'-m-phenylene-bis-(2-oxazoline), 2,2'-m-phenylene-bis-(4,4'-dimethyl-2-oxazoline), bis-(2-oxazolinylcyclohexane)sulfide, and bis-(2-oxazolinylnorbornane)sulfide.
7. The biosensor according to claim 1, wherein the crosslinking agent comprises at least one selected from the group consisting of 2-vinyl-2-oxazoline, 2-vinyl-4-methyl-2-oxazoline, 2-vinyl-5-methyl-2-oxazoline, 2-isopropenyl-2-oxazoline, 2-isopropenyl-4-methyl-2-oxazoline, and 2-isopropenyl-5-ethyl-2-oxazoline.
8. The biosensor according to claim 1, wherein the electrically conductive macromolecule comprises at least one selected from the group consisting of polypyrrole, polyaniline, polystyrene sulfonate, polythiophene, polyisothianaphthene, and polyethylene dioxythiophene(poly(3,4-ethylenedioxythiophene)poly(styrenesulfonate)).
9. The biosensor according to claim 1, wherein the detection layer comprises a sugar.
10. The biosensor according to claim 1, wherein the detection layer comprises at least one sugar selected from the group consisting of a disaccharide, a trisaccharide, a tetrasaccharide, a pentasaccharide, and a hexasaccharide.

11. The biosensor according to claim 1, wherein the detection layer comprises at least one sugar selected from the group consisting of xylobiose, agarobiose, carrabiose, maltose, isomaltose, sophorose, cellobiose, trehalose, neotrehalose, isotrehalose, inulobiose, vicianose, isoprimeverose, sambubiose, primeverose, solabiose, melibiose, lactose, lycobiose, epicellobiose, sucrose, turanose, maltulose, lactulose, epigentibiose, robinobiose, silanobiose, and rutinose.

12. The biosensor according to claim 1, wherein the detection layer comprises at least one sugar selected from the group consisting of glucosyl trehalose, cellotriose, chacotriose, gentianose, isomaltotriose, isopanose, maltotriose, manninotriose, melezitose, panose, planteose, raffinose, soratriose, and umbelliferose.

13. The biosensor according to claim 1, wherein the detection layer comprises at least one sugar selected from the group consisting of maltosyl trehalose, maltotetraose and stachyose.

14. The biosensor according to claim 1, wherein the detection layer comprises at least one sugar selected from the group consisting of maltotriosyl trehalose, maltopentaose, verbascose, and maltohexaose.

* * * * *